United States Patent
Mahajan et al.

(12)

(10) Patent No.: US 6,444,695 B1
(45) Date of Patent: Sep. 3, 2002

(54) INHIBITION OF THROMBIN-INDUCED PLATELET AGGREGATION BY CREATINE KINASE INHIBITORS

(75) Inventors: Vinit Mahajan, Rancho Palos Verdes; Dennis D. Cunningham; Sadashiva Pai, both of Irvine, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/960,822

(22) Filed: Sep. 21, 2001

Related U.S. Application Data (60) Provisional application No. 60/234,875, filed on Sep. 21, 2000.

(51) Int. Cl.$^7$ .............................................. A61K 31/415
(52) U.S. Cl. ...................................................... 514/398
(58) Field of Search ........................................ 514/398

(56) References Cited

U.S. PATENT DOCUMENTS

| | | | |
|---|---|---|---|
| 5,091,404 A | 2/1992 | Elgebaly ..................... | 514/401 |
| 5,321,030 A | 6/1994 | Kaddurah-Daouk et al. ..... | 514/275 |
| 5,324,731 A | 6/1994 | Kaddurah-Daouk et al. ..... | 514/275 |
| 5,585,361 A | 12/1996 | Burns et al. ................... | 514/25 |
| 5,676,978 A | 10/1997 | Teicher et al. ............... | 424/649 |
| 5,720,956 A | 2/1998 | Rohdewald .............. | 424/195.1 |
| 5,998,457 A | 12/1999 | Kaddurah-Daouk et al. ..... | 514/392 |
| 6,028,087 A | 2/2000 | Bondinell et al. ........... | 514/357 |
| 6,075,031 A | 6/2000 | Kaddurah-Daouk et al. ..... | 514/275 |
| 6,129,932 A | 10/2000 | Asgharnejad et al. ........ | 424/489 |
| 6,268,380 B1 | 7/2001 | Tjoeng et al. .............. | 514/318 |

FOREIGN PATENT DOCUMENTS

| | | |
|---|---|---|
| WO | 90/09192 | 8/1990 |
| WO | 92/08456 | 5/1992 |
| WO | 94/16687 | 8/1994 |

OTHER PUBLICATIONS

Annesley, et al., "Cyclocreatine Phosphate As a Substitute For Creatine Phosphate in Vertebrate," Biochem. Biophys. Res. Commun., vol. 74, pp. 185–190 (1977).

Donovan, et al., "Thrombin Induces Apoptosis in Cultured Neurons and Astrocytes Via a Pathway Requiring Tyrosine Kinase and RhoA Activities," J. Neuroscience, vol. 17(14) pp. 5316–5326 (1997).

Griffiths, et al., "Accumulation of Analog of Phosphocreatine in Muscle of Chicks Fed 1–Carboxymethyl–2–iminoidazolidine (Cyclocreatine)," J. Biol. Chem., vol. 251, pp. 2049–2054 (1976).

Kristensten, et al., "Creatine and Cyclocreatine Treatment of Human Colon Adenocarcinoma Xenografts: $^{31}$P and $^1$H Magnetic Resonance spectroscopic Studies," Br. J. Cancer, vol. 79(2), pp. 278–85 (1999).

Lin, et al., "Determination of the Catalytic Site of Creatine Kinase by Site–Directed Mutagenesis," Biochim. Biophys. Acta, vol. 1206, pp. 97–104 (1994).

Liu, et al., "Inhibitory Effect of Disodium Quercetin–7, 4'–Disulfate on Aggregation of Pig Platelets Induced by Thrombin and its Mechanism," Institute of Biochemistry and Molecular Biology, Guangdong Medical College, Acta Pharmacol. Sin., 21(8), 737,741, (2000), Abstract Only.

Liu, et al., "Inhibitory Effects of Sodium Quercetin Monosulfate on Pig Platelet Aggregation Induced by Thrombin," Institute of Medical Biochemistry, Department of Chemistry, Guangdong Medical College, Zhongguo Yaoli Xuebao, 20(7), 623–626 (1999) Abstract Only.

Lowe, et al., "Evidence for an Associative Mechanism in the Phosphoryl Transfer Step Catalyzed by Rabbit Muscle Creatine Kinase," J. Biol. Chem., vol. 225, No. 9, pp. 3944–3951 (1980).

Matthews, et al., "Neuroprotective Effects of Creatine and Cyclocreatine in Animal Models of Huntington's Disease," J. Neuroscience, vol. 18(1), pp. 156–163 (No date Available).

McLaughlin, et al., "Specificity of Creatine Kinase for Guanidino Substrates," J. Biol. Chem., vol. 247, pp. 4382–4388 (1972).

Mahajan, et al., "Creatine Kinase, an ATP–Generating Enzyme, is Required for Thrombin Receptor Signaling to the Cytoskeleton," PNAS, 97:22, pp. 12062–12067 (Oct. 24, 2000).

Miller, et al., "Inhibition of Rate of Tumor Growth by Creatine and Cyclocreatine," PNAS, vol. 90, pp. 3304–08 (1993).

Nguyen, A. C. K., "Synthesis and Enzyme Studies Using Creatine Analogues," Thesis, Department of Pharmaceutical Chemistry, University of California, San Francisco, (1983).

(List continued on next page.)

*Primary Examiner*—Raymond Henley, III
(74) *Attorney, Agent, or Firm*—Christie, Parker & Hale, LLP (57) ABSTRACT

Methods of using creatine compounds such as creatine kinase inhibitors, and more particularly, cyclocreatine and homocyclocreatine, to inhibit thrombin-induced cytoskeletal reorganization, platelet aggregation, inflammatory processes, endothelial cell contraction and related cardiovascular and CNS disorders are described. Pharmaceutically effective amounts of creatine compounds are administered to subjects in need thereof to thereby prevent and/or treat diseases and/or pathological conditions such as thrombosis, thrombocytopenia, atherosclerosis, coronary artery disease, unstable angina pectoris, myocardial infarction, stroke, coagulopathies, and transient ischemia attacks.

51 Claims, 7 Drawing Sheets

OTHER PUBLICATIONS

Roberts, et al., "Synthesis and Accumulation of an Extremely Stable High–Energy Phosphate Compound by Muscle, Heart, and Brain of Animals Fed the Creatine Analog, 1–Carboxyethyl–2–iminoimidazolidine (Homocyclocreatine)," Arch. Biochem. Biophy., vol. 220, pp. 563–571 (1983).

Roberts, et al., "Higher Homolog and N–Ethyl Analog of Creatine as Synthetic Phosphagen Precursors in Brain, Heart, and Muscle, Repressors of Liver Amidinotransferase, and Substrates for Creatine Catabolic Enzymes," J. Biol. Chem., vol. 260, pp. 13502–13508 (1995).

Rowley, et al., "On the Specificity of Creatine Kinase. New Glycocyamines and Glycocyamine Analogs Related to Creatine," J. Am. Chem. Soc., vol. 93:20, pp. 5542–5551 (1971).

Teicher, et al., "Cyclocreatine in Cancer Chemotherapy," Cancer Chemotherapy Pharmacology, vol. 35, pp. 411–416 (1995).

Ubl, et al., "Characteristics of Thrombin–Induced Calcium Signals in Rat Astrocytes," GLIA, vol. 21, pp. 361–369 (1997).

Wallimann, et al., "Intracellular Compartmentation, Structure and Function of Creatine Kinase Isoenzymes in Tissues with High and Fluctuating Energy Demands: The 'Phosphocreatine Circuit' for Cellular Energy Homeostasis," Biochem. J., vol. 281, pp. 21–401 (1992).

INHIBITION OF THROMBIN-INDUCED PLATELET AGGREGATION BY CREATINE KINASE INHIBITORS

CROSS-REFERENCE TO RELATED APPLICATION(S)

This application claims the benefit of U.S. Provisional Application, Ser. No. 60/234,875, filed Sep. 21, 2000, the contents of which are hereby incorporated by reference in their entirety.

STATEMENT REGARDING FEDERALLY SPONSORED RESEARCH OR DEVELOPMENT

This invention was made with Government support under Grant No. AG00538, awarded by the National Institutes of Health. The Government has certain rights in this invention.

FIELD OF THE INVENTION

The present invention relates to a new method of use for creatine compounds such as creatine kinase inhibitors and, more particularly, cyclocreatine, to block intracellular signals of the thrombin receptor Protease Activated Receptor-1, to thereby inhibit thrombin-induced cytoskeletal reorganization, platelet aggregation and endothelial cell contraction.

BACKGROUND OF THE INVENTION

Platelets are discoid cells found in large numbers in blood, which are important for blood coagulation and hemostasis. Upon activation by various stimuli like thrombin, thromboxane $A_2$ and ADP, platelets change into a spheroid shape with filopodia, degranulate and aggregate. Platelet activation is important for hemostasis and underlies various pathological conditions such as unstable angina pectoris, myocardial infarction, stroke, and coagulopathies. One of the physiological agents that activate platelets is thrombin, a serine protease. Thrombin mediates its action through the activation of protease activated receptors (PARs). Cytoskeletal rearrangement and shape changes precede platelet aggregation following thrombin receptor activation. Thrombin mediates vascular permeability, morphological changes in neurons and astrocytes through activation of PAR-1. Two thrombin receptors, high affinity PAR-1 and low affinity PAR-4, have been identified on human platelets. Low concentrations (1 nM) of thrombin activates PAR-1 in human platelets, while complete activation of platelets require higher amounts (>10 nM) of thrombin and activation of PAR-4.

Endothelium forms a barrier between blood and underlying tissues in the vascular system. Vascular endothelium actively participates in regulating vascular tone, inflammation, haemostasis and thrombosis. Endothelial cells express and release a repertoire of molecules that regulate vascular as well as endothelial function. During vascular injury and in inflammation thrombin released from the blood activates thrombin receptors (PARs) expressed on endothelial surface. Thrombin and thrombin receptors regulate various endothelial functions and play a pivotal role in vascular development and in the response of endothelial cells to vascular injury. Thrombin released during vascular injury has diverse effects on endothelial cells. Thrombin induces cytoskeletal changes resulting in cell rounding. Contraction of endothelial cells leads to increased permeability and compromises in the endothelial barrier. Thrombin also causes endothelial cells to proliferate during vascular injury. Endothelial cells release various vasoactive substances during wound healing in the presence of thrombin. High affinity thrombin receptor, PAR-4, is not expressed on endothelial cells and, therefore, most of the thrombin responses in endothelial cells are PAR-1 mediated.

PAR-1 mediates the cellular responses to thrombin during blood coagulation, cell proliferation, vascular permeability changes, tumor metastasis, and nervous system injury. PAR-1 is a seven-transmembrane G protein-coupled receptor with a novel activation mechanism. Proteolysis at a thrombin cleavage site in the extracellular amino terminus exposes a new amino terminus containing the peptide ligand SFLLRN, which binds intramolecularly to initiate intracellular signals. Although originally detected in platelets, endothelial cells, and fibroblasts, PAR-1 is also expressed in the nervous system in a developmentally regulated manner and by specific subpopulations of neurons and astrocytes that are especially vulnerable to neurodegeneration and ischemic injury.

In most cells expressing PAR-1, activation of the receptor transmits signals to the actin cytoskeleton that profoundly alter cell shape. Platelets, for example, convert from a spherical to disk shape and extend filopodia, endothelial cells contract, neurons retract axons, and astrocytes resorb processes and flatten their cell bodies. These signals also regulate changes in actin-related cell motility observed in neurons, fibroblasts, and tumor cells. The morphological response is mediated by a key signaling pathway that uses serine/threonine kinases, G12/13, RhoA, and myosin light chain kinase; actomyosin contraction generates tension through the formation of stress fibers and focal adhesions. There are several points along this signal transduction pathway at which high-energy phosphate in the form of ATP is required. Only phosphorylated myosin is capable of interacting with actin filaments, and actin polymerization requires binding to ATP. Depletion of total cellular ATP or the application of drugs that block the ATP binding sites of serine-threonine kinases, for example, inhibits PAR-1-mediated shape changes. Activation of G12/13 requires phosphorylation and a ready supply of GTP. Thus, the actomyosin contraction underlying cellular shape changes is an active, energy-consuming process where localized ATP homeostasis is critical.

Creatine kinase enzymes regulate ATP homeostasis in subcellular compartments by the transfer phosphates between creatine and adenine nucleotides. The mitochondrial isoform generates creatine phosphate, which is shuttled to cytosolic isoforms strategically localized to specific subcellular regions where they provide ATP at sites of high and fluctuating energy demand. In sea urchin sperm, for example, mitochondrial creatine kinase is restricted to sperm heads whereas cytosolic creatine kinase is expressed in the sperm tail, and specifically inhibiting ATP generation by the cytosolic creatine kinase results in defective tail movements and sperm motility. The cytosolic muscle isoform localizes along the M-line to the myosin heads where it provides ATP during actomyosin contraction. The cytosolic brain isoform (CKB) and its insect homolog arginine kinase localize to the membranes of neurons and astrocytes and are concentrated along axons and moving lamellipodial edges of migrating glia, although the precise function of CKB is not known.

The creatine kinase/creatine phosphate system is an energy generating system operative predominantly in the brain, muscle, heart, retina, adipose tissue and the kidney. Wallimann et al., *Biochem. J.*, 281: 21–401 (1992). The components of the system include the enzyme creatine kinase (CK), the substrates creatine, creatine phosphate (CrP), ATP, ADP, and the creatine transporter. Creatine kinase is a phosphotransferase, which catalyzes reversibly at localized intracellular sites the transfer of a phosphoryl group from creatine phosphate to ADP to generate ATP which is the main source of energy in the cell. CK plays a key role in the energy homeostasis of cells with intermittently high, fluctuating energy requirements, like neurons, and photoreceptor, and muscle cells. CK is expressed in a tissue specific manner: CK-M (muscle form) and CK-B (brain form). CK is localized in discrete cellular compartments coupled functionally to sites of energy production (glycolysis and mitochondria) or energy consumption (actomyosin ATPase and $Ca^{++}$-ATPase).

Some of the functions associated with CK/CrP system include efficient regeneration of energy in the form of ATP in cells with fluctuating and high energy demand, energy transport to different parts of the cell, phosphoryl transfer activity, ion transport regulation, and involvement in signal transduction pathways.

The substrate creatine is a compound that is naturally occurring and is found in mammalian brain, skeletal muscle, retina, adipose tissue and the heart. The phosphorylated form, creatine phosphate, is also found in the same organs and is the product of the creatine kinase reaction. Both compounds can be easily synthesized and are non-toxic to humans and animals. A series of creatine analogs, including cyclocreatine, homo cyclocreatine and β-guanidino propionic acid, have been synthesized and shown to be efficacious for combating viral infections (U.S. Pat. No. 5,321,030); for inhibiting growth, transformation, or metastasis of mammalian cells (U.S. Pat. Nos. 5,324,731 and 5,676,978); for treatment of obesity (U.S. Pat. No. 5,998,457); and for the prevention and treatment of glucose metabolic disorders (U.S. Pat. No. 6,075,031), which are expressly incorporated herein by reference in their entireties. The use of cyclocreatine for restoring functionality in muscle tissue is disclosed in U.S. Pat. No. 5,091,404. PCT publication No. WO 94/16687 describes a method for inhibiting the growth of several tumors using creatine and related compounds. No prior work has established a direct link between the creatine kinase system and diseases related to thrombin induced cytoskeletal reorganization, platelet aggregation, inflammatory processes, endothelial cell contraction and related cardiovascular and CNS disorders.

SUMMARY OF THE INVENTION

The present invention is directed to a new method of use for creatine compounds such as creatine kinase inhibitors, and more particularly, cyclocreatine and homocyclocreatine, to inhibit thrombin-induced cytoskeletal reorganization, platelet aggregation, inflammatory processes, endothelial cell contraction and related cardiovascular and CNS disorders.

Because these creatine compounds, and particularly creatine kinase inhibitors, modulate intracellular signals of the thrombin receptor PAR-1, creatine compound treatment may be applied in vivo to inhibit pathological platelet aggregation and endothelial cell barrier function.

Cyclocreatine, a competitive inhibitor of creatine kinase, may be taken orally or given intravenously for hypercoaguable, platelet, inflammatory, cardiovascular or cerebrovascular diseases, disorders and conditions. Other known therapies, involving the administration of non-steroidal anti-inflammatory drugs (NSAIDS) such as aspirin, may cause problems with ulceration and bleeding in the stomach. Cyclocreatine may not have the same side effects associated with NSAIDS and other platelet inhibitors.

In practice of the invention, pharmaceutically effective amounts of creatine compounds are administered to subjects in need thereof to thereby prevent and/or treat diseases and/or pathological conditions such as thrombosis, thrombocytopenia, atherosclerosis, coronary artery disease, unstable angina pectoris, myocardial infarction, stroke, coagulopathies, and transient ischemia attacks.

Creatine compounds can also be used to coat devices such as vascular grafts, stents or valves to be placed in contact with blood, to thereby prevent aggregation on the device.

BRIEF DESCRIPTION OF THE DRAWINGS

(A) Yeast two-hybrid -galactosidase filter lift assay summary. PAR-1 cytoplasmic loops (CL1, CL2, CL3) and C-tail fused with a GAL4 DNA binding domain (DB) were coexpressed with partial cDNA clones encoding either CKB fused to a GAL4 activation domain (AD) or the AD vector alone. A positive interaction was only detected between the PAR-1 C-tail and CKB.

(B) Pull-down assay shows specific interaction between $^{35}$S-labeled CKB and GST-C-tail fusion protein but not GST alone. Autoradiograph (AR).

(C) Pull-down assay using purified CKB. Immunoblot (IB) with anti-CKB antibody.

(D) CKB activity detection after immunoprecipitation (IP) with control IgG (lane 1) or with anti-PAR-1 antibodies (lane 2) from primary astrocyte cultures.

(E) CKB protein coimmunoprecipitates with anti-PAR-1 antibodies (lane 2, arrowhead) but not control IgG (lane 1), or anti-PAR-1 antibodies preadsorbed with antigenic peptide SFLLRN (lane 3). Ig heavy chain (*).

(A) Schematic of GST-C-tail truncation mutants (Top). Pull-down assay shows $^{35}$S-labeled CKB binds to GST-C-tail mutant 382–420 (lane 3) but not to mutant 382–408 (lane 4) or 382–399 (lane 5) (Middle). Coomassie blue stain of GST and GST-C-tail fusion proteins (Bottom). Autoradiograph (AR).

(B) Schematic of wild-type CKB (WT) and mutants (Upper). Autoradiograms displaying $^{35}$S-labeled CKB mutants (Left) and their binding to GST-PAR-1 C-tail fusion protein in pull-down assays (Right).

(A) Vehicle-treated cells display a stellate morphology.

(B) Thrombin treatment (10 pM) converts cells to a flat, nonstellate morphology.

(C) CKB antisense alone has no effect.

(D) CKB antisense treatment blocks thrombin morphology effects.

(E) Results were quantified as the percent stellate astrocytes, mean± SEM., n=3; asterisk denotes P<0.005. (Inset) CKB immunoblot shows CKB expression levels and specificity of antisense knockdown. Vehicle (V), CKB antisense (AS), and control oligonucleotides: CKB reverse sequence (R) and CKB RNaseH-insensitive oligonucleotides (RI).

(A) Vector transfected cells are round and refractile.

(B) Thrombin (T, 160 nM) flattens cells.

(C) DN-CKB transfected cells are refractile.

(D) Cells expressing DN-CKB remain refractile after thrombin treatment and do not flatten, whereas surrounding untransfected cells become flat.

(E) Results were quantified as the percent transfected cells with refractile morphology, mean±SD, n=3; asterisk denotes P<0.001.

(F) Cyclocreatine (CCr) protects astrocytes from thrombin (10 pM) induced shape changes in a dose-dependent manner. Results are mean±SD, n=3; P<0.001.

(A) Thrombin-activated GTP-RhoA (Upper) shows reduced levels with cyclocreatine treatment; RhoA levels (Lower) in total lysate (representative immunoblots, n=3).

(B) Immunoblot (IB) of RhoA in solubilized astrocyte membranes after various treatments (Upper); cyclocreatine (CCr). The relative amount of membrane RhoA was quantitated densitometrically as the percent RhoA in control cells (Lower), mean±SD, n=3; asterisk denotes P<0.001.

(C) CKB inhibition does not affect PAR-1-mediated increases in $[Ca^{2+}]_i$. Representative experiment displays the kinetics of $[Ca^{2+}]_i$ flux monitored with the FLIPR detection system in astrocytes after thrombin addition (10 pM, T), cyclocreatine (50 mM), or phospholipase C inhibitor (1 $\mu$M, U-73122). Peak calcium changes were quantitated and normalized to control (Inset), mean±SD, n=3.

FIG. 6 is a schematic diagram illustrating the PAR-1 signaling pathways: Creatine kinase-B (CKB) interacts with the cytoplasmic tail (C-tail) of the PAR-1 thrombin receptor, where it may provide bursts of site-specific high energy phosphate and activating RhoA, a small protein that relays signals to the cytoskeleton (G-12/13 Signaling Pathway). Cyclocreatine, a creatine analog that inhibits CKB, blocks thrombin-induced cytoskeletal reorganization and platelet aggregation. A second signaling pathway, involving the PAR-1 cytoplasmic loop-2 (CL-2), does not appear to be affected by cyclocreatine (G-q Pathway). PLC=phospholipase C; MLC=myosin light chain; GTP=guanosine 5'-triphosphate; GDP=guanosine diphosphate; P=phosphate.

A. Cyclocreatine treatment inhibits cytoskeletal changes in human umbilical vein endothelial cells (HUVEC) in response to thrombin.

B. Cell rounding effect of thrombin was quantitated (n=4) and is protected by cyclocreatine in a dose-responsive manner.

C. The change in calcium levels does not significantly differ after cyclocreatine or geldanamycin treatment.

D. Peak fluorescence from 3–4 separate experiments was measured. There were no significant changes when HUVECs were treated with cyclocreatine (CCr) or geldanamycin (GA). A phospholipase inhibitor U-73122 and ET18-OCH$_3$ completely abolished blocks calcium changes as did thapsigargin (thaps), an intracellular calcium depletion agent.

DETAILED DESCRIPTION OF THE INVENTION

The present invention relates to a new method of use for creatine compounds such as creatine kinase inhibitors and, more particularly, cyclocreatine and homocyclocreatine, to block intracellular signals of the thrombin receptor Protease Activated Receptor-1 (PAR-1), to thereby inhibit thrombin-induced cytoskeletal reorganization, platelet aggregation and endothelial cell contraction.

Creatine Kinase Regulates Thrombin/PAR-1 Mediated Cytoskeletal Reorganization in Platelets and Endothelial Cells The present inventors hypothesized that molecules necessary for the early stages of thrombin signaling might bind to the intracellular face of PAR-1. To examine this, a yeast two-hybrid screen was performed, uncovering an interaction between the PAR-1 cytoplasmic tail (C-tail) and the cytosolic brain isoform of creatine kinase (CKB). Because the muscle isoform of creatine kinase delivers a burst of compartmentalized ATP for contracting skeletal muscle and is linked to actomyosin function in various cells, the present inventors hypothesized that CKB may perform a similar function during PAR-1-directed cytoskeletal reorganization. Using three different methods to ablate CKB activity, the inventors found that CKB was necessary for PAR-1 signal transduction to the cytoskeleton. Mahajan, et al., (2000) PNAS 97: 12062–12067 is hereby incorporated by reference in its entirety.

Materials. The protein-protein interaction screen was performed by using the Matchmaker GAL4 two-hybrid system and a rat brain cDNA library (CLONTECH). Rabbit anti-PAR-1 antibody was a gift from M. Runge (University of Texas Medical Branch, Galveston), anti-CKB antibodies were obtained from Chemicon, and anti-RhoA was from Santa Cruz Biotechnology. CKB activity was measured with CK 520 Sigma. ATP levels were measured with the bioluminescent somatic cell assay (Sigma FL-ASC). Thrombin and purified CKB were purchased from Calbiochem, and cyclocreatine was purchased from Sigma. Site-directed mutagenesis was performed with Quick Change (Stratagene). G. Molloy (Delaware University) graciously provided the CKB plasmid, and T. Ma (Baylor College, Houston) provided the dominant negative CKB mutant. Statistical analysis was carried out by using two-way ANOVA.

Yeast Two-Hybrid Interaction. The PCR product of rat PAR-1 C-tail (residues 382–431) and oligonucleotides for human PAR-1 cytoplasmic loops CL-1 (residues 119–135), CL-2 (residues 199–218), and CL-3 (residues 289–311) were cloned into the GAL4 DNA-binding (DB) vector pAS2-1. These bait plasmids were used in a yeast two-hybrid screen to probe a rat brain cDNA library fused to a GAL4 activation domain (AD) in pGAD10 by cotransformation into Y190 yeast. Positive clones were selected on Leu/Trp/His plates and by detection of -galactosidase activity using a filter lift method (CLONTECH). Interactions were confirmed by retransforming positive clones either with bait vector or the original pAS2-1 vector (backbone) into yeast.

Glutathione S-Transferase (GST) Pull-Down Assays. The rat PAR-1 C-tail was subcloned into a GST vector, and the mutant fusions were constructed by introducing stop codons D400Z, Q409Z, and H421Z. Fusion proteins were purified by using glutathione-Sepharose beads (Amersham Pharmacia). CKB truncation mutants were constructed by introducing stop codons into pGEM-1/rat CKB at amino acids Q185Z, K298Z, and K358Z. CKB mutant 186–297 was generated by PCR and cloned into pGEM-1. CKB constructs were expressed and labeled with [35S] methionine/cysteine (Amersham Pharmacia) by using a rabbit reticulocyte lysate expression system (TNT T7, Invitrogen). Binding studies were performed overnight at 4° C. with 25 µl of washed glutathione beads and 30–50 pg of either GST or GST-PAR-1 C-tail fusion protein in 200 µl of 25 mM Hepes, pH 7.5, 100 mM NaCl, 50 mM KCl, 5 mM MgCl2, 1 mM DTT, 10% glycerol, 1% Nonidet P-40, 0.2% BSA. Binding products were separated by SDS/PAGE and analyzed by autoradiography or immunoblots with anti-CKB antibodies and enhanced chemiluminescence (Amersham Pharmacia).

Coimmunoprecipitation. Primary cortical astrocyte cultures were prepared from 1- to 2-day-old Sprague-Dawley rats as described in Donovan, et al., (1997) *J. Neurosci.* 17: 5316–5326. Astrocytes were solubilized and incubated with control antibody (rabbit IgG) or anti-PAR-1 antibody overnight at 4° C. in the presence of protein A-Sepharose. Immunoprecipitation products were either subjected to CKB activity assays or separated by SDS/PAGE and analyzed on immunoblots with anti-CKB antibodies.

Astrocyte Morphology Studies. Oligonucleotides based on a CKB antisense sequence (GUGUCUGCAACAGCUUAGC-CAUCAG), a control reverse sequence (GACUACCGAUUCGACAACGUCUGUG), and an identical antisense sequence rendered insensitive to RNaseH were purchased from Sequitur (Natick, Mass.) and transformed into primary astrocyte cultures with Lipofectin (GIBCO/BRL) for 1 h. After 18 h, cells were differentiated in 1.5 mM dibutyryl cAMP for 2 h. A total of 10 pM thrombin was added for 2 h for a maximal response, and the morphology of approximately 200 cells was examined under phase-contrast micrography and scored as either stellate or flat. Antisense knockdown of CKB was confirmed by immunoblot analysis. Morphology assays were also performed after a 4-h treatment with 50 mM cyclocreatine.

Dominant Negative CKB Studies. The dominant negative CKB mutant C283S, described in Lin, et al., (1994) *Biochim. Biophys. Acta* 1206: 97–104, was cloned into the pIRES-EGFP vector (CLONTECH) and transfected for 6 h with Novafector (VennNova, LCC) into Ad12HER10 retinoblasts seeded into Lab-Tek II slides (Nunc). After 18 h, cells were differentiated with 2 mM dibutyryl cAMP in serum-free medium for 6 h. After addition of thrombin (160 nM) for 2 h, transfected cells (20–30%) were identified by fluorescence micrography, and the cell morphology of approximately 100 transfected cells was examined with phase-contrast illumination and scored blind to treatment as either refractile or flat.

RhoA Activation and Translocation Assay. Active RhoA levels were measured in primary rat astrocytes as described in Ren, et al., (1999) *EMBO J*. 18: 578–585. Astrocytes received a 4-h 50 mM cyclocreatine treatment before the thrombin (10 pM) addition for 10 min. Cell lysates were incubated with GST-Rhotekin binding domain (20–30 µg) for 45 min, washed, and immunoprobed with anti-RhoA antibody. For membrane RhoA, crude membrane fractions were prepared as described in Donovan, et al., (1997) *J. Neurosci.* 17: 5316–5326. Fifteen micrograms of membrane protein fractions was separated by SDS/PAGE and immunoblotted with anti-RhoA antibody.

Intracellular Calcium Assay. Astrocytes were treated with or without 50 mM cyclocreatine for 4 h. Cell medium was decanted and replaced with Fluo-3 AM (Molecular Probes) for 1 h. Some wells received 1 µM U-73122 (Biomol, Plymouth Meeting, Pa.) for 10 min before 10 pM thrombin and 10 mM EDTA injection. The relative intracellular calcium levels were monitored at 488 nM for 210 sec in 4–8 identically treated wells by using a Fluorometric Imaging Plate Reader (Molecular Devices).

PAR-1 Interacts with CKB in Vitro and in Vivo. Membrane receptors depend on specific contacts selectively made with effector molecules to create intracellular signals. To identify molecular components required for PAR-1 signal transduction, the 51-amino acid segment corresponding to the rat PAR-1 C-tail was used to probe approximately $3.5 \times 10^6$ cDNAs from a rat brain cDNA library for binding partners in a yeast two-hybrid screen. Eight colonies representing putative interactions were detected between the PAR-1 C-tail and cDNAs in a -galactosidase filter lift assay. Nucleotide sequencing and comparison to sequences in the GenBank database revealed that the cDNA from a single colony encoded amino acids 185–381 of CKB. The CKB interaction was specific to the C-tail and was not detected with CL-1, -2, -3 or with the vectors alone (FIG. 1A).

This interaction was confirmed in a GST pull-down assay in which full-length $^{35}$S-labeled CKB was incubated with either GST or a GST-PAR-1 C-tail fusion protein. Analysis of binding products by SDS/PAGE and autoradiography revealed that $^{35}$S-labeled CKB bound only the GST-C-tail fusion and not GST alone (FIG. 1B).

Figure 1:
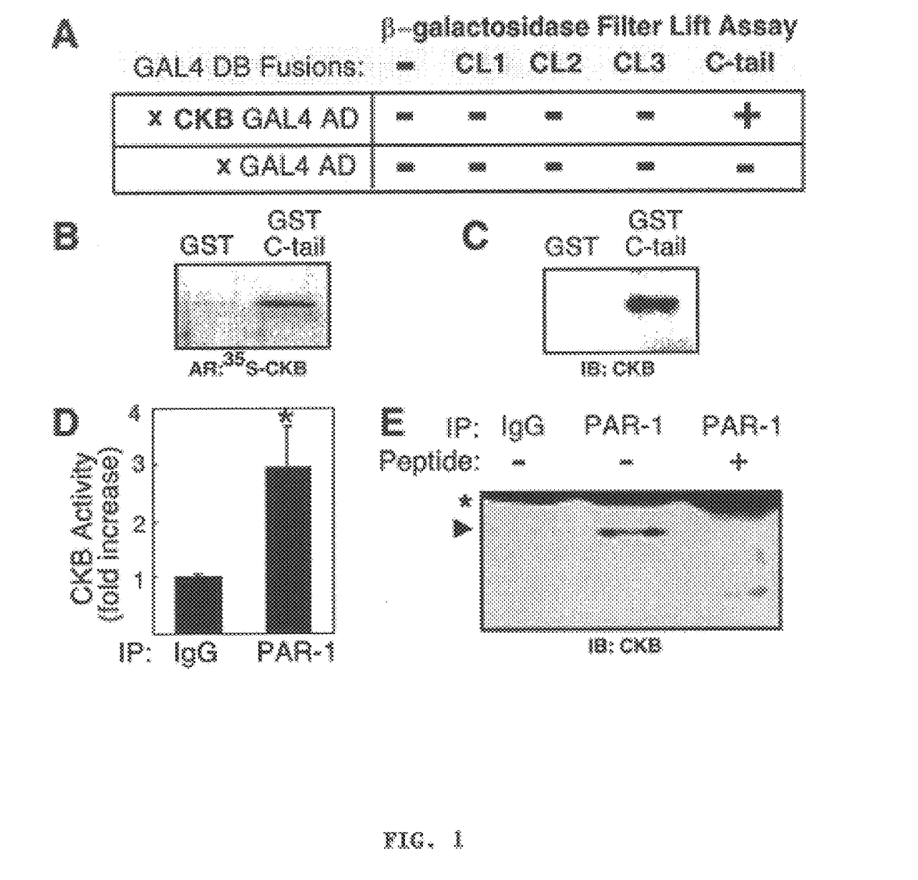
FIG. 1 shows the interaction of CKB with PAR-1.

In a separate binding experiment using human brain-purified CKB, a specific interaction with GST-C-tail was also observed (FIG. 1C). The yeast two-hybrid and in vitro binding studies suggested PAR-1 may directly interact with CKB through its C-tail.

To determine whether PAR-1 was bound to CKB under physiological conditions, PAR-1 antibodies were tested to determine whether they would co-immunoprecipitate CKB from primary cultures of rat astrocytes. Antibody complexes were affinity purified and analyzed for the presence of CKB using a highly specific and sensitive CKB calorimetric enzyme assay. We detected more than a 3-fold higher level of CKB activity in PAR-1 immunoprecipitates as compared with control IgG precipitates (FIG. 1D).

To further confirm the interaction, PAR-1 immunoprecipitates were separated by SDS/PAGE and analyzed for the presence of CKB. Immunoblots against CKB demonstrated that anti-PAR-1 antibodies specifically coprecipitated CKB because CKB did not coprecipitate with control serum or with anti-PAR-1 antibodies preadsorbed with its antigenic SFLLRN peptide (FIG. 1E). The CKB signal comigrated with the CKB band detected in rat brain extracts (data not shown).

Figure 2:
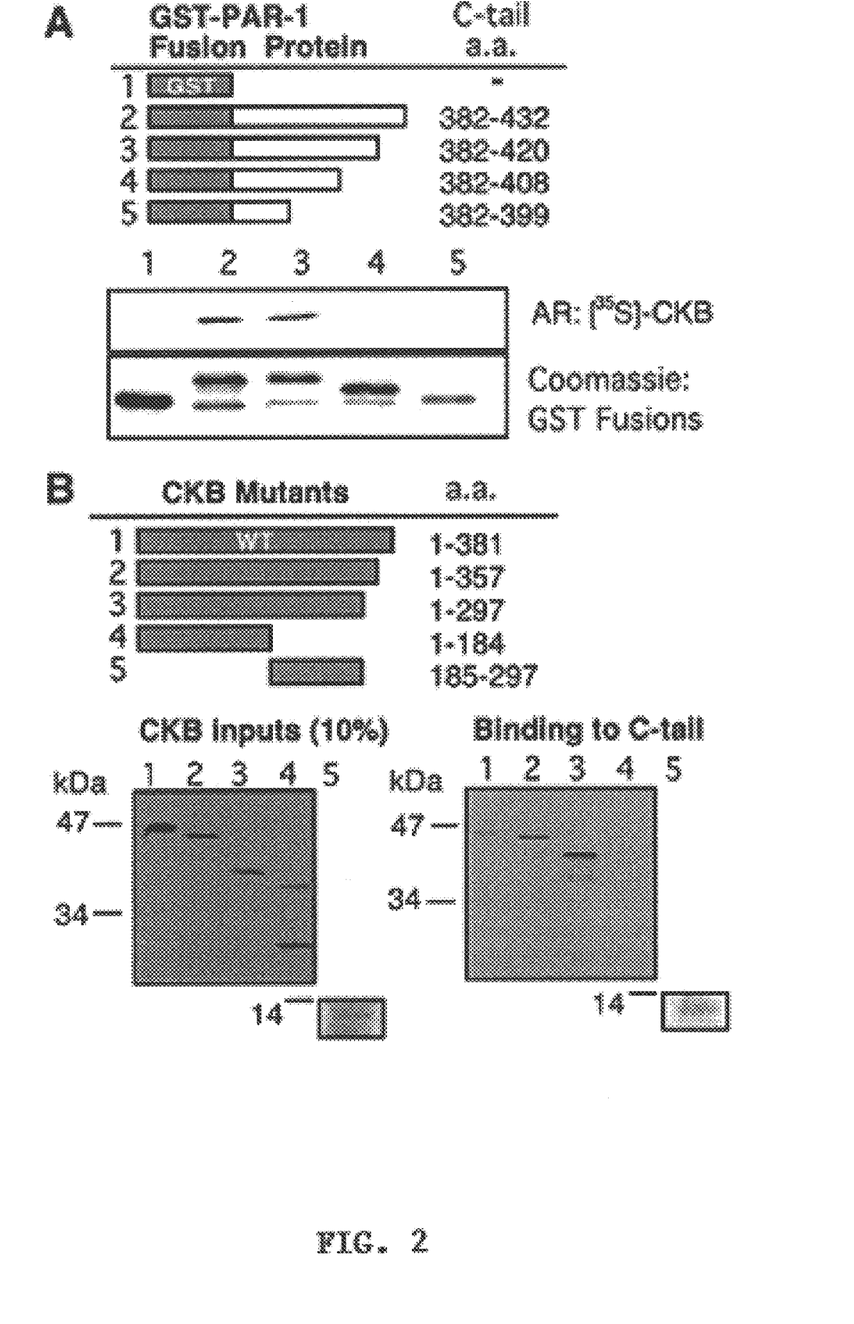
FIG. 2 shows a domain analysis of PAR-1 association with CKB.

Mutational Analysis Identifies PAR-1 and CKB Interaction Domains. To identify segments of the C-tail required for the CKB interaction, GST fusions to PAR-1 C-tail truncation mutants were generated. These mutants were analyzed for their ability to bind metabolically labeled CKB. $^{35}$S-labeled CKB bound C-tail mutant 382–420 in which the last 12 amino acids were removed. Binding was abolished, however, with further deletions in C-tail mutants 382–408 and 382–399. This suggests that the intervening C-tail region 408–420 was important for the CKB interaction (FIG. 2A).

The C-tail amino acids 408–420 (GQLMPSKMDTCSS) partially overlap with sequences potentially important for receptor internalization. A series of CKB truncation mutants were designed to locate domains important for the interaction with the PAR-1 C-tail. Interestingly, the inventors found that by deleting the last 24 or 84 amino acids, the interaction of CKB mutants 1-357 and 1–297 with the C-tail was enhanced. The last 24–84 amino acids contain domains that distinguish CKB from other creatine kinase isoforms.

No binding was detected with CKB mutant 1–184, which encompassed the amino-terminal region absent from the original yeast two-hybrid clone. On the other hand, the intervening CKB amino acid sequence 185–297 was sufficient for the interaction (FIG. 2B); this region is highly conserved between species and tissue isoforms and contains residues important for enzymatic catalysis. None of the CKB mutants bound GST alone (data not shown). Together, the binding studies revealed a specific in vitro interaction between the PAR-1 C-tail and CKB that persisted in vivo and raised the possibility that CKB may play a role in PAR-1 signaling.

CKB Antisense Prevents Thrombin-Mediated Shape Changes in Astrocytes. PAR-1-mediated changes in cellular structure are easily observed in the highly polarized shapes of astrocytes where cell bodies flatten and long cellular processes are resorbed. Primary cultures of astrocytes normally display a stellate shape characterized by a round, refractile cell body with numerous processes (FIG. 3A).

Figure 3:
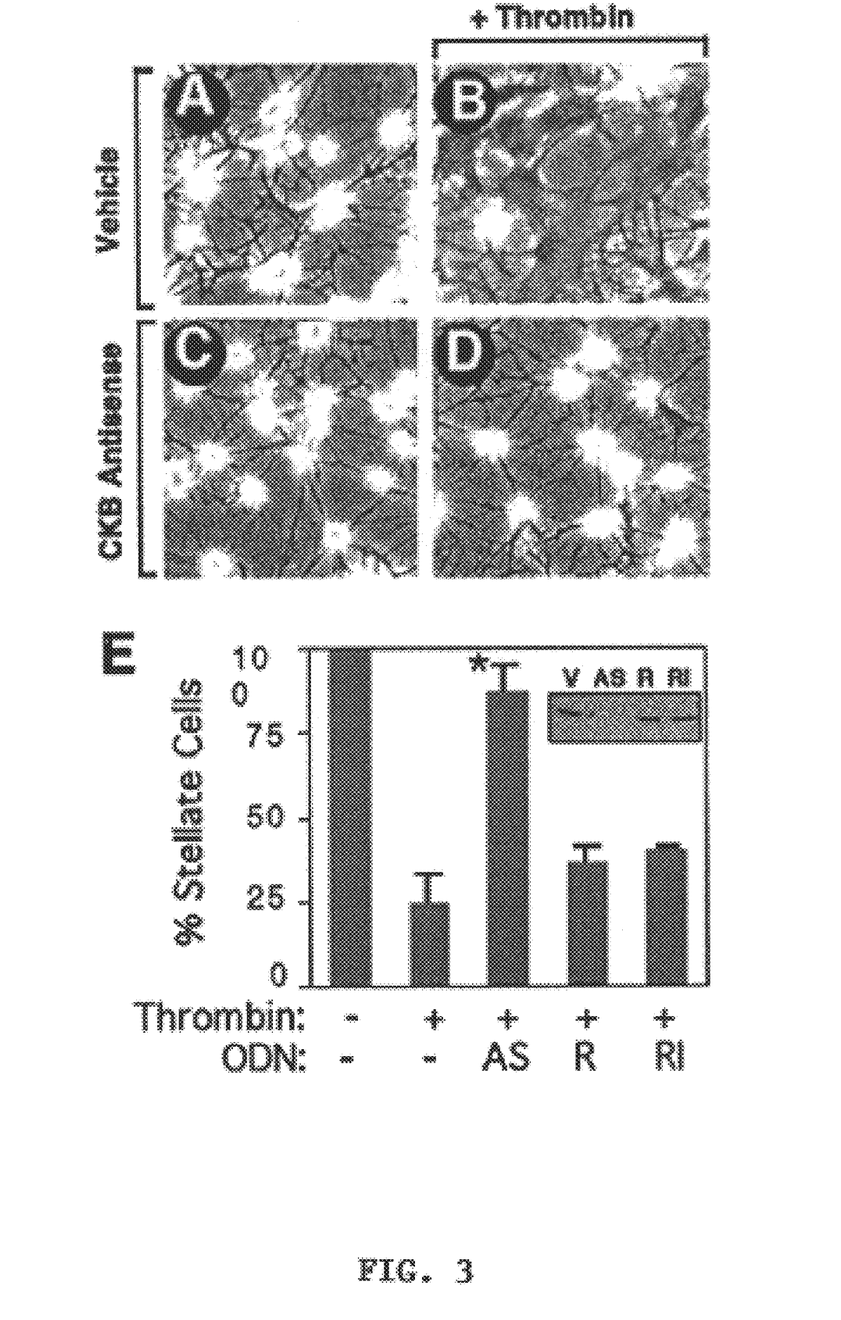
FIG. 3 shows that CKB antisense oligonucleotides prevent thrombin-induced morphological response in astrocytes.

Upon PAR-1 activation by thrombin, most cells flattened and resorbed processes (FIG. 3B). To test whether CKB was required for the cytoskeletal response, the inventors transfected an antisense oligonucleotide (ODN) directed toward the 3' end of the CKB mRNA to knockdown CKB expression. Similar antisense strategies have been previously applied successfully to creatine kinase.

Astrocytes treated with CKB antisense ODNs expressed significantly lower levels of CKB detected by Western blot (FIG. 3E) without affecting cell morphology (FIG. 3C). When challenged with thrombin, antisense-treated astrocytes no longer responded, and more than a 3-fold greater number of cells maintained a stellate morphology (FIG. 3D).

The observed effect was not due to total ATP depletion as CKB antisense treatment did not affect total cellular ATP levels or cell viability, and no changes in actin expression levels were noted in immunoblots (data not shown). The specificity of the antisense effect was confirmed with control ODNs. The antisense ODN was modified with 2'-O-methyl groups such that it retains its ability to bind target sequences but is no longer a substrate for RNaseH, making it an extremely rigorous control for nonspecific ODN effects. Neither a reverse sequence ODN (Rev) nor the ODN rendered insensitive to RNaseH had any significant effect on CKB expression or on PAR-1-mediated morphological effects (FIG. 3E). An unrelated ODN with similar GC content had no effect either (data not shown). These results support a role for CKB in PAR-1-mediated cytoskeletal regulation.

Dominant Negative CKB Blocks Shape Changes in Retinoblasts. The next question addressed was whether the catalytic activity of CKB was necessary during the PAR-1 signal. Cytosolic creatine kinase is a dimer that catalyzes the reversible transfer of phosphate from phosphocreatine to ADP in the reaction: phosphocreatine+ADP creatine+ATP. Expression of dominant negative CKB in which the highly conserved cysteine-283 residue near the active site is mutated to serine diminishes enzymatic activity.

A plasmid expressing a bicistronic mRNA encoding dominant negative CKB and an enhanced green fluorescent protein reporter gene (EGFP) was transfected into human neuronal retinoblast cells (Ad12HER10) and the effect on PAR-1 signaling was observed. The response to thrombin in these human neuronal cells has been extensively characterized and was especially suited for transfecting human CKB constructs.

Figure 4:
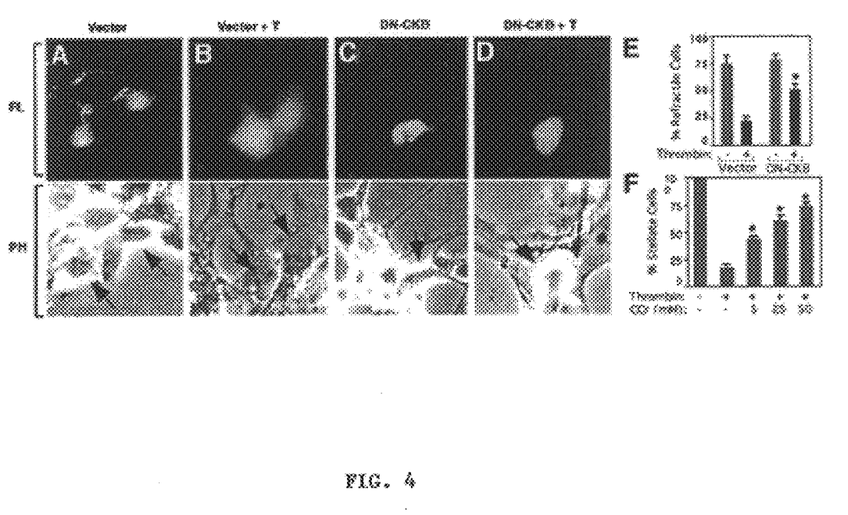
FIG. 4 shows the reduction in CKB activity by dominant negative CKB (DN-CKB) expression or cyclocreatine blocks thrombin-mediated morphological changes. Transiently transfected retinoblasts were identified under fluorescence microscopy (FL) by the expression of enhanced green fluorescent protein reporter gene (Upper). Morphology of the corresponding cells (Lower; arrows) was examined under phase-contrast microscopy (PH).

Most cells expressing EGFP vector alone displayed round retractile cell bodies (FIG. 4A). These spherical cell bodies under phase contrast illumination appear surrounded by a bright white halo. Upon thrombin treatment, cells appeared nonrefractile, becoming flattened with increased cell body diameters (FIG. 4B).

Retinoblasts expressing dominant negative CKB appeared similar to controls (FIG. 4C); these cells, however, did not flatten in response to thrombin, leaving more than a 2-fold greater number of cells with a round and refractile shape (FIG. 4D).

Thus, catalytically active CKB was required to transmit the full effect of PAR-1 morphology signals. Retinoblast morphology responses were similarly inhibited by overexpression of the C-tail or C-tail peptides overlapping the CKB binding regions, whereas overexpression of CL-2 had no effect (unpublished observations).

Cyclocreatine Inhibits Thrombin-Mediated Shape Changes. The necessity for CKB enzymatic activity was further supported in experiments using the creatine analog, cyclocreatine. Although the analog is readily phosphorylated to phosphocyclocreatine, it is a very poor phosphate donor and specifically reduces ATP production by CKB.

Astrocytes treated with cyclocreatine displayed a dose-dependent decrease in their morphological response to thrombin that was phenotypically identical to the CKB antisense knockdown treatment. Although most stellate-shaped astrocytes flattened and resorbed processes in response to thrombin, up to a 4-fold greater number of astrocytes remained stellate in the presence of cyclocreatine (FIG. 4E). Cyclocreatine also blocked the thrombin/PAR-1 morphological response in Ad12HER10 retinoblasts (data not shown). Cyclocreatine had no effect on total ATP levels or cell viability (data not shown).

CKB Is Necessary for RhoA Activation But Not Calcium Signals. The next step was to determine in which PAR-1 second-messenger pathways CKB might act. The Rho family of small GTP-binding proteins relays signals from PAR-1 to the actin cytoskeleton. After PAR-1 activation, RhoA is activated with the exchange of GDP for GTP and translocates to the membrane where the sequential activation of Rho kinase, myosin light chain kinase, and myosin light chain stimulate actomyosin contraction.

To determine whether CKB activity was required in this PAR-1 pathway, astrocytes were treated with cyclocreatine and activated RhoA was measured in a pull-down assay using GST-rhotekin that only interacts with activated GTP-RhoA. GST alone did not pull down GTP-RhoA (data not shown).

Figure 5:
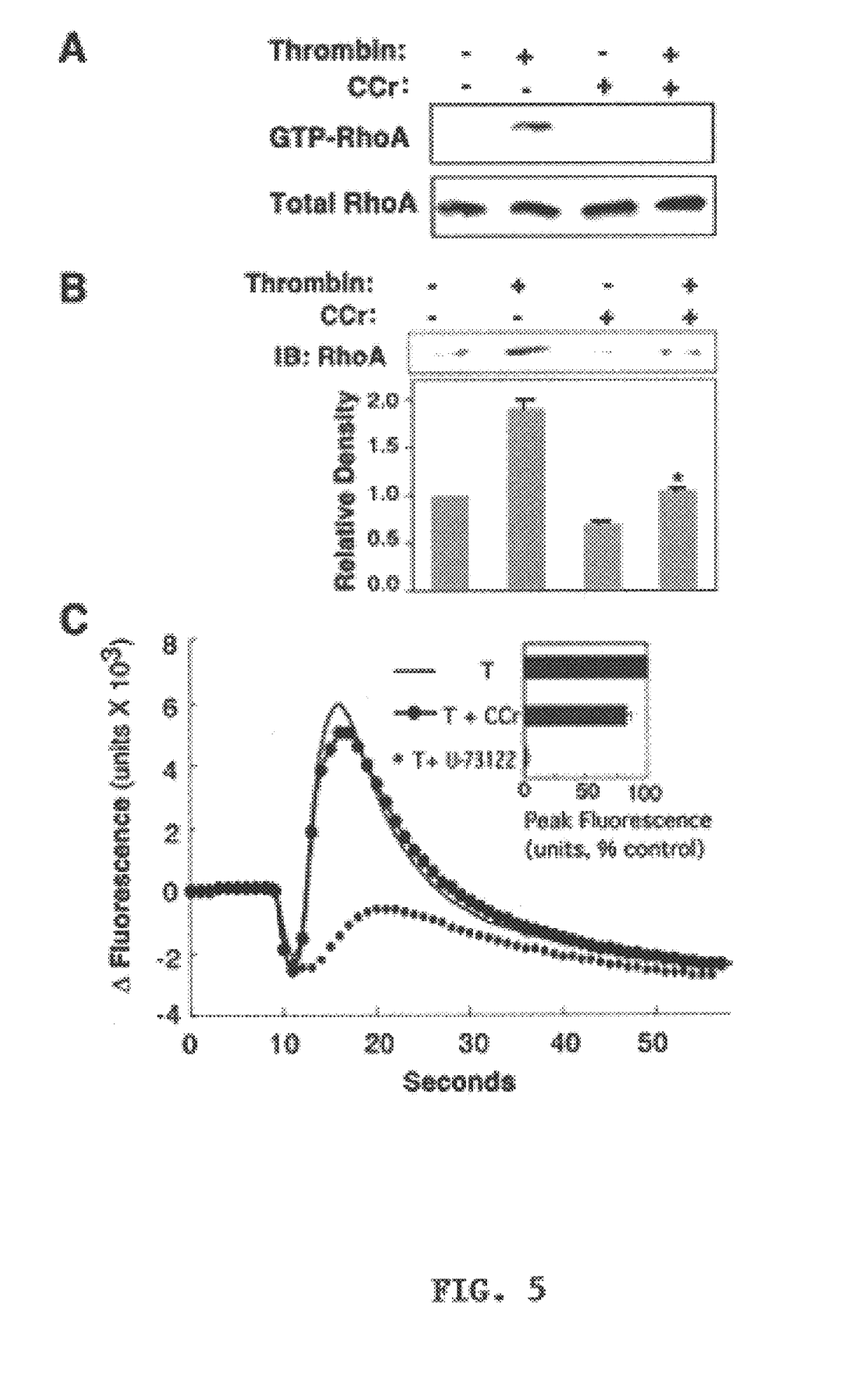
FIG. 5 shows that CKB inhibition blocks PAR-1-mediated RhoA activation and translocation to the membrane but not $[Ca^{2+}]_i$ flux.

The application of cyclocreatine significantly reduced GTP-RhoA after thrombin treatment (FIG. 5A). RhoA levels nearly double at the membrane after thrombin treatment (FIG. 5B). In the presence of cyclocreatine, membrane RhoA levels were similar to controls; however, there was almost no translocation after thrombin treatment (FIG. 5B). No changes in cytosolic levels of RhoA were observed, suggesting only a small fraction of RhoA translocates to the membrane in comparison to cytosolic levels (data not shown). These experiments suggest that CKB is necessary for RhoA activation and translocation to the membrane.

PAR-1 also activates phospholipase C, which leads to a rapid release of calcium from intracellular stores, and inhibition of this second messenger system has no effect on thrombin-mediated cytoskeletal reorganization. The calcium signal is mediated through the PAR-1 CL2 and does not require the C-tail.

Because CKB does not bind CL2, the inventors hypothesized that calcium signals may be independent of CKB. Intracellular calcium levels in astrocytes were monitored with the indicator dye Fluo-3. As expected, thrombin elicited a robust calcium peak observed within seconds that could be inhibited by the application of phospholipase C inhibitor (U-73122) as described in Ubl, J. & Reiser, G. (1997) Glia 21: 361–369.

Application of cyclocreatine to inhibit CKB activity left the calcium response to thrombin largely intact, and cells displayed only a minor decline in peak intracellular calcium (FIG. 5C). Therefore, CKB seemed less important for the calcium second-messenger pathway.

Discussion. The present inventors identified an interaction between the PAR-1 C-tail and CKB in a yeast two-hybrid screen, and this interaction was confirmed in vitro and in vivo. Mutational studies suggested the interaction was specific and could be localized to distinct domains of CKB and the PAR-1 C-tail. Among seven-transmembrane receptors, the C-tail is one of the least conserved regions, and several mutational studies emphasize its role during receptor signaling.

Although the precise functions of PAR-1 intracellular segments are not known, the intracellular calcium release pathway was previously shown to depend on the PAR-1 CL-2 and not on its C-tail. The PAR-1 C-tail is required for receptor down-regulation, and recent studies demonstrate that a C-tail truncation mutant led to defects in chemotaxis. Thus, as with the -adrenergic receptor and prostaglandin E receptor subtype EP3, the C-tail may help direct one of several independent signaling pathways through specific effector interactions.

By the targeted reduction of CKB activity through three different mechanistic approaches, the efficiency of PAR-1 signals to the cytoskeletal was reduced. CKB antisense, dominant negative CKB, and competitive substrate inhibition with cyclocreatine all produced similar phenotypes. Although each method has its limitations and potential nonspecific effects, all together they support a model in which CKB is important for PAR-1 morphological signals. None of the treatments was toxic to cells nor did any treatment affect total ATP levels. Moreover, the continued presence of calcium signals after thrombin treatment strongly suggests that CKB inhibition does not disturb cell viability or thrombin signal transduction in general. This is consistent with the results of other antisense, dominant negative, knockout, and cyclocreatine studies where creatine kinase serves as a subcellular, compartmentalized regulator of ATP homeostasis rather than pancellular generator of ATP such as oxidative phosphorylation.

PAR-1 calcium signals are mediated through CL2 and Gq activation. This pathway is distinct from a second PAR-1 pathway mediated by G12/13 and RhoA that leads to actomyosin contractions underlying changes in cell morphology. The inventors' studies support the concept that two separate signaling pathways emanate from PAR-1 and suggest that the C-tail may direct a G12/13 and RhoA pathway in which CKB activity is critical. The PAR-1-CKB interaction identified in these studies may also be important during other RhoA pathway-dependent thrombin signals that regulate cell viability, vascular endothelial permeability, platelet aggregation, and fibroblast stress fiber formation. CKB is also expressed in endothelium, platelets, and fibroblasts where PAR-1 mediates morphological responses. Preliminary studies by the inventors suggest a similar CKB signaling mechanism may persist in these cells (unpublished observations).

The present inventors studies suggest that PAR-1 may incorporate an ATP generating system into its signal transduction machinery by promoting a specific interaction with CKB through its C-tail. This would provide high-energy phosphate during cytoskeletal reorganization precisely at the membrane site of receptor signaling, where ATP homeostasis is critical for localized protein phosphorylation, actin polymerization, and actomyosin contraction. Mislocalization of otherwise enzymatically normal glycolytic enzymes, for example, is sufficient to disrupt normal actomyosin contractility and underscores the importance of site-specific subcellular energy generation. Because the dominant negative mutant is probably capable of binding to PAR-1, it is likely that localized ATP generation is a critical factor in signal generation. A role for creatine kinase during cellular shape changes and cell motility is supported by studies that showed creatine kinase-muscle knockout mice display altered contractility patterns. Also, creatine kinase inhibitors reduce tumor cell motility, and the creatine kinase homolog arginine kinase is selectively concentrated in motile versus static neuronal growth cones.

Why certain cellular reactions are preferentially coupled to ATP generated specifically by creatine kinase as opposed to other ATP generating systems remains enigmatic, although metabolite channeling within multienzyme complexes and the energetic advantage of the close apposition of creatine kinase to ATPases demonstrated in previous studies is an attractive explanation. An explicit function for creatine kinase during signal transduction is suggested by the recently demonstrated interaction with AMP-activated protein kinase and regulation of its kinase activity. CKB might also regulate protein kinases during PAR-1 signaling where shape changes are, in fact, inhibited by the application of drugs that block the ATP binding sites of serine-threonine kinases, although the precise kinases for thrombin signaling are yet to be identified.

Use of Creatine Kinase Inhibitors to Inhibit Thrombin-Induced Platelet Aggregation Prior to the present invention, the creatine kinase-B system had not been implicated in platelets and endothelial cells. The present inventors have found that PAR-1 interacts with CKB, which regulates thrombin/PAR-1 mediated cytoskeletal reorganization in platelets and endothelial cells.

Figure 6:
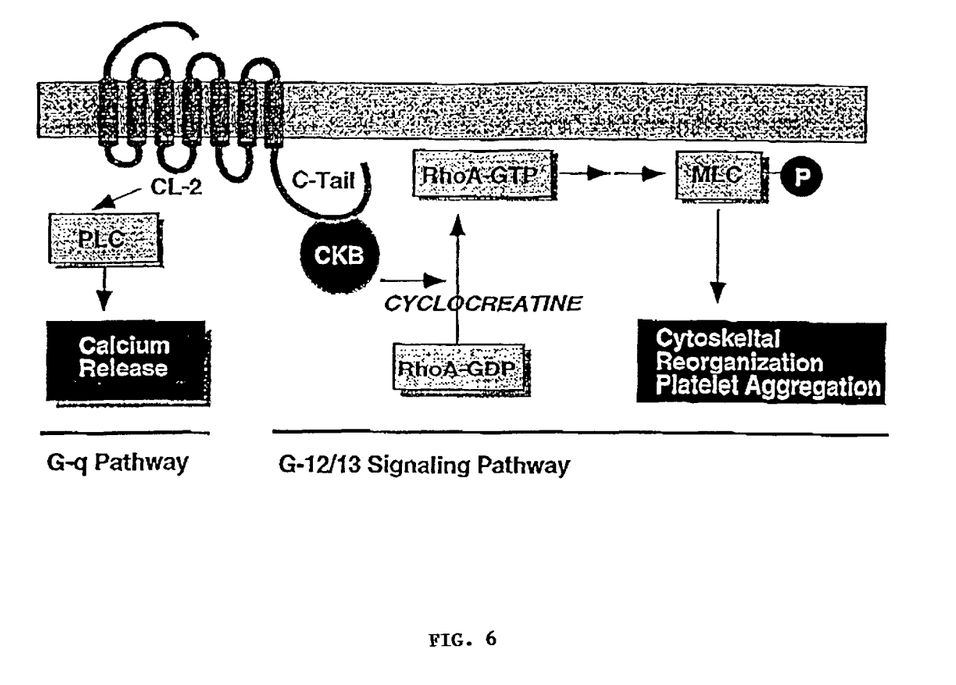

CKB provides an ATP source from creatine phosphate to cells at localized sites to meet high-energy demands. See FIG. 6, illustrating the PAR-1 signaling pathway. As illustrated in FIG. 6, ATP provided by CKB may be used to activate RhoA, a small G-protein, which, along with its downstream effectors, are an established signaling pathway in platelets, as well as in vascular endothelial cells.

Importantly, the present inventors have found that thrombin/PAR-1 cytoskeletal signaling can be blocked by inhibition of CKB. Thus, the present invention also provides a new method of use for creatine compounds that modulate one or more of the structural or functional components of the creatine kinase/creatine phosphate system to block intracellular signals of the thrombin receptor PAR-1, to thereby inhibit thrombin-induced cytoskeletal reorganization, platelet aggregation, inflammatory processes, endothelial cell contraction and related cardiovascular and CNS disorders. One class of creatine compounds particularly useful in the present invention are creatine kinase inhibitors such as cyclocreatine and homocyclocreatine.

The method of the present invention generally comprises administering to an individual afflicted with or susceptible to a disease or pathological condition involving thrombin-induced cytoskeletal reorganization, platelet aggregation, inflammatory processes, endothelial cell contraction and related cardiovascular and CNS disorders, an amount of a creatine compound, such as a creatine kinase inhibitor, sufficient to prevent, reduce or ameliorate symptoms of the disease or pathological condition.

Such diseases and pathological conditions include, but are not limited to, thrombosis, thrombocytopenia, atherosclerosis, coronary artery disease, unstable angina pectoris, myocardial infarction, stroke, coagulopathies, and transient ischemia attacks. Other diseases, disorders and pathological conditions involving thrombin-induced cytoskeletal reorganization, platelet aggregation, inflammatory processes, endothelial cell contraction and related cardiovascular and CNS disorders are known in the art.

The method of the present invention can also used in association with the implantation of prosthetic devices to inhibit thrombosis and for promoting reperfusion of an artery or vein and inhibiting reocclusion.

By treatment is meant the amelioration or total avoidance of the platelet or endothelial cells related disorder mentioned herein. By prevention is meant the avoidance of a currently recognized disease state in a patient evidencing disorders described above.

Components of the CK/CrP system which can be modulated include the CK enzyme, the substrates creatine, creatine phosphate, ADP, ATP, and the transporter of creatine. As used herein, the term "modulate" means to change, affect or interfere with the function of the component in the CK/CrP enzyme system. Creatine analogues, for example, modulate the CK/CrP system by inhibiting the CK enzyme. Examples of creatine analogues include cyclocreatine, homocyclocreatine and β-guanidino propionic acid.

Compounds that are particularly effective for use in the present invention include cyclocreatine, homocyclocreatine, creatine phosphate and analogues thereof which are described below. The term "creatine compound" will be used herein to include creatine, creatine phosphate, cyclocreatine, homocyclocreatine, compounds which are structurally similar to creatine, creatine phosphate, cyclocreatine and homocyclocreatine, and analogues of creatine, creatine phosphate, cyclocreatine and homocyclocreatine.

The term "creatine compound" also includes compounds which "mimic" the activity of cyclocreatine and creatine phosphate or creatine analogues i.e., compounds which modulate the creatine kinase system. The term "mimics" is intended to include compounds which may not be structurally similar to creatine but mimic the therapeutic activity of the creatine analogues cyclocreatine and creatine phosphate or structurally similar compounds.

The term creatine compounds will also include inhibitors of creatine kinase, i.e. compounds which inhibit the activity of the enzyme creatine kinase, molecules that inhibit the creatine transporter or molecules that inhibit the binding of the enzyme to other structural proteins or enzymes or lipids.

The term "modulators of the creatine kinase system" are compounds which modulate the activity of the enzyme, or the activity of the transporter of creatine, or the ability of the enzyme to associate with other cellular components. These could be substrates for the enzyme and they would have the ability to build in their phosphorylated state intracellularly. These types of molecules are also included in the term creatine compounds.

The term creatine "analogue" is intended to include compounds which are structurally similar to creatine such as cyclocreatine and creatine phosphate, compounds which are recognized in the art as being analogues of creatine, and/or compounds which share the same function as cyclocreatine and creatine phosphate.

Creatine (also known as N-(aminoiminomethyl)-N-methyl glycine; methylglycosamine or N-methyl-guanidinoacetic acid) is a well-known substance. See, The Merck Index, Eleventh Edition No. 2570 (1989). Creatine is phosphorylated chemically or enzymatically by creatine kinase to generate creatine phosphate, which is also well known (see, The Merck Index, No. 7315). Both creatine and creatine phosphate (phosphocreatine) can be extracted from animals or tissue or synthesized chemically. Both are commercially available.

Cyclocreatine is an essentially planar cyclic analogue of creatine. Although cyclocreatine is structurally similar to creatine, the two compounds are distinguishable both kinetically and thermodynamically. Cyclocreatine is phosphorylated efficiently by the enzyme creatine kinase in the forward reaction, both in vitro and in vivo. It represents a class of substrate analogues of creatine kinase and which are believed to be active.

Several creatine compounds have been previously synthesized for other purposes. See, e.g., Rowley et. al., *J. Am. Chem. Soc.*, 93:5542–5551 (1971); Mclaughlin et. al., *J. Biol. Chem.*, 247:4382–4388 (1972); Nguyen, A. C. K., "Synthesis and enzyme studies using creatine analogues", Thesis, Department of Pharmaceutical Chemistry, Univ. of Calif., San Francisco, (1983); Lowe et al., *J. Biol. Chem.*, 225:3944–3951 (1980); Roberts et. al., *J. Biol. Chem.*, 260:13502–13508 (1995); Roberts et. al., *Arch. Biochem. Biophy.*, 220:563–571 (1983), and Griffiths et. al., *J. Biol. Chem.*, 251:2049–2054 (1976). The contents of all of the aforementioned references are expressly incorporated herein by reference. Further to the aforementioned references, Kaddurah-Daouk et. al., (WO 92108456; WO 90/09192; U.S. Pat. Nos. 5,324,731; 5,321,030) also provide citations for the synthesis of a plurality of creatine analogues. The contents of all the aforementioned references and patents are hereby incorporated herein by reference.

It is possible to modify the substances described herein to produce analogues which have enhanced characteristics, such as greater specificity for the enzyme, enhanced solubility or stability, enhanced cellular uptake, or better binding activity. Salts of products may be exchanged to other salts using standard protocols.

Bisubstrate analogues of creatine kinase and non hydrolyzable substrate analogues of creatine phosphate (non transferable moieties which mimic the N phosphoryl group of creatine phosphate) can be designed readily and would be examples of creatine kinase modulators. Creatine phosphate compounds can be synthesized chemically or enzymatically. The chemical synthesis is well known. Annesley, I M., Walker, J. B., *Biochem. Biophys. Res. Commun.*, 74:185–190 (1977); Cramer, F., Scheiffele, E., Vollmar, A., *Chem. Ber.*, 95:1670–1682 (1962).

Creatine compounds which are useful in this invention include those described in U.S. Pat. No. 6,075,031, encompassed by the following general formula:

and pharmaceutically acceptable salts thereof, wherein:
a) Y is selected from the group consisting of: —$CO_2H$—, —NHOH, —$NO_2$, —$SO_3H$, —C(=O)$NHSO_2J$ and —P(=O) (OH) (OJ), wherein J is selected from the group consisting of hydrogen, $C_1$–$C_6$ straight chain alkyl, $C_3$–$C_6$ branched alkyl, $C_2$–$C_6$ alkenyl, $C_3$–$C_6$ branched alkenyl, and aryl;
b) A is selected from the group consisting of: C, CH, $C_1$–$C_5$ alkyl, $C_2$–$C_5$ alkenyl, $C_2$–$C_5$ alkynyl, and $C_1$–$C_5$ alkoyl chain, each having 0–2 substituents which are selected independently from the group consisting of:
  1) K, where K is selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of bromo chloro, epoxy and acetoxy;
  2) an aryl group selected from the group consisting of a 1–2 ring carbocycle and a 1–2 ring heterocycle, wherein the aryl group contains 0–2 substituents, independently selected from the group consisting of —$CH_2L$ and —$COCH_2L$ where L is independently selected from the group consisting of bromo, chloro, epoxy and acetoxy; and
  3) —NH—M, wherein M is selected from the group consisting of hydrogen, $C_1$–$C_4$ alkyl, $C_2$–$C_4$ alkenyl, $C_1$–$C_4$ alkoyl, $C_3$–$C_4$ branched alkyl, $C_3$–$C_4$ branched alkenyl, and $C_4$ branched alkoyl;
c) X is selected from the group consisting of $NR_1$, $CHR_1$, $CR_1$, O and S, wherein $R_1$ is selected from the group consisting of:
  1) hydrogen;
  2) K, where K is selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of: bromo, chloro, epoxy and acetoxy;
  3) an aryl group selected from the group consisting of a 1–2 ring carbocycle and a 1–2 ring heterocycle, wherein the aryl group contains 0–2 substituents independently selected from the group consisting of —$CH_2L$ and —$COCH_2L$ where L is independently selected from the group consisting of bromo, chloro, epoxy and acetoxy;
  4) a $C_5$–$C_9$ α-amino-ω-methyl-ω-adenosylcarboxylic acid attached via the (ω-methyl carbon;
  5) 2 $C_5$–$C_9$ α-amino-ω-aza-ω-methyl-ω-adenosylcarboxylic acid attached via the ω-methyl carbon; and
  6) a $C_5$–$C_9$ α-amino-ω-thia-ω-methyl-ω-adenosylcarboxylic acid attached via the ω-methyl carbon;
d) $Z_1$ and $Z_2$ are chosen independently from the group consisting of: =O, —$NHR_2$, —$CH_2R_2$, —$NR_2OH$;

wherein $Z_1$ and $Z_2$ may not both be =O and wherein $R_2$ is selected from the group consisting of:
1) hydrogen;
2) K, where K is selected from the group consisting of: $C_1$–$C_6$ straight alkyl; $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of: bromo, chloro, epoxy and acetoxy;
3) an aryl group selected from the group consisting of a 1–2 ring carbocycle and a 1–2 ring heterocycle, wherein the aryl group contains 0–2 substituents independently selected from the group consisting of: —$CH_2L$ and —$COCH_2L$ where L is independently selected from the group consisting of: bromo, chloro, epoxy and acetoxy;
4) 2 $C_4$–$C_8$ α-amino-carboxylic acid attached via the ω-carbon;
5) B, wherein B is selected from the group consisting of —$CO_2H$, —NHOH, —$SO_3H$, —$NO_2$, OP(=O) (OH) (OJ) and —P(=O)(OH)(OJ), wherein J is selected from the group consisting of hydrogen, $C_1$–$C_6$ straight alkyl, $C_3$–$C_6$ branched alkyl; $C_2$–$C_6$ alkenyl, $C_3$–$C_6$ branched alkenyl, and aryl, wherein B is optionally connected to the nitrogen via a linker selected from the group consisting of $C_1$–$C_2$ alkyl, $C_2$ alkenyl, and $C_1$–$C_2$ alkoyl;
6)-D-E, wherein D is selected from the group consisting of $C_1$–$C_3$ straight alkyl, $C_3$ branched alkyl, $C_2$–$C_3$ straight alkenyl, $C_3$ branched alkenyl, $C_1$–$C_3$ straight alkoyl, aryl and aroyl; and E is selected from the group consisting of —(PO$_3$)n-NMP, where n is 0–2 and NMP is ribonucleotide monophosphate connected via the 5'-phosphate, 3'-phosphate or the aromatic ring of the base; —[p (=O) ($OCH_3$) (O)]m-Q, where m is 0–3 and Q is a ribonucleoside connected via the ribose or the aromatic ring of the base; —[P(=O) (OH) ($CH_2$)]m-Q, where m is 0–3 and Q is a ribonucleoside connected via the ribose or the aromatic ring of the base; and an aryl group containing 0–3 substituents chosen independently from the group consisting of Cl, Br, epoxy, acetoxy, —OG, —C(=O)G, and —$CO_2G$, where G is independently selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, $C_4$–$C_6$ branched alkoyl, wherein E may be attached to any point to D, and if D is alkyl or alkenyl, D may be connected at either or both ends by an amide linkage; and
7)-E, wherein E is selected from the group consisting of —(PO$_3$)n-NMP, where n is 0–2 and NMP is a ribonucleotide monophosphate connected via the 5'-Phosphate, 3'-phosphate or the aromatic ring of the base; —[P(=O)($OCH_3$) (O)]m-Q, where m is 0–3 and Q is a ribonucleoside connected via the ribose or the aromatic ring of the base; —[P(=O) (OH) ($CH_2$)]m-Q, where m is 0–3 and Q is a ribonucleoside connected via the ribose or the aromatic ring of the base; and an aryl group containing 0–3 substituents chosen independently from the group consisting of Cl, Br, epoxy, acetoxy, —OG, —C(=O)G, and —$CO_2G$, where G is independently selected from the group consisting of $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, $C_4$–$C_6$ branched alkoyl; and if E is aryl, E may be connected by an amide linkage;

e) if $R_1$ and at least one $R_2$ group are present, $R_1$ may be connected by a single or double bond to a $R_2$ group to form a cycle of 5 to 7 members;

f) if two $R_2$ groups are present, they may be connected by a single or a double bond to form a cycle of 4 to 7 members; and g) if $R_1$ is present and $Z_1$ or $Z_2$ is selected from the group consisting of —$NHR_2$, $CH_2R_2$ and —$NR_2OH$, then $R_1$ may be connected by a single or double bond to the carbon or nitrogen of either $Z_1$ or $Z_2$ to form a cycle Of 4 to 7 members.

Currently preferred compounds include cyclocreatine, homocyclocreatine, creatine phosphate and those compounds included in Tables 1 and 2 of the '031 patent.

The modes of administration for these compounds include, but are not limited to, oral, transdermal, transmucosal (e.g., sublingual, nasal, vaginal or rectal) or parenteral (e.g., subcutaneous, intramuscular, intravenous, bolus or continuous infusion). The actual amount of drug needed will depend on factors such as the size, age and severity of disease in the afflicted individual.

Creatine has been administered to athletes in the range of 2–8 gms/day to improve muscle function. Creatine phosphate was administered to patients with congestive heart failure also in the range of several gm/day, and was very well tolerated. In experimental animal models of cancer or viral infections, where creatine compounds have been shown to be active, amounts of 1 gm/kg/day were administered intravenously or intraperitoneally.

Creatine dosages in humans, as a oral supplement, typically follow a 20 g/day (or 0.3 g/kg) loading dose for five days, followed by a maintenance dose of 2 g/day (or 0.03 g/kg). Skeletal muscle has a creatine storage capacity of 150 to 160 mmol/kg (normal is 125 mmol/kg), so excess creatine is simply excreted. These dosage values are comparable to dosages of cyclocreatine, a competitive inhibitor of CK, used in rat studies, which typically vary between 0.5 to 1.0 g/kg (given intravenously) or 150 mg to 1 g, administered orally. See Miller et al., (1993) PNAS 90:3304–08; Teicher et al., (1995) *Cancer Chemotherapy Pharmacology* 35: 411–416; Kristensten et al., (1999) *Br. J. Cancer* 79: 278–85; and Mathews et al., *J. Neuroscience* 18: 156–63, all of which are hereby incorporated by reference in their entirety.

For this invention the creatine compound will be administered at dosages and for periods of time effective to reduce, ameliorate or eliminate the symptoms of the disease or pathological condition. Dose regimens may be adjusted for purposes of improving the therapeutic or prophylactic response of the compound. For example, several divided doses may be administered daily, one dose, or cyclic administration of the compounds to achieve the desired therapeutic result. Agents that improve the solubility of these compounds could also be added.

Dosages of creatine compounds such as cyclocreatine and homocyclocreatine pharmaceutically effective in inhibiting platelet aggregation, thereby preventing thrombus formation, are believed to be about 1 mg/kg bodyweight to about 500 mg/kg bodyweight per day, and preferably about 10 mg/kg to about 100 mg/kg per day. When administered in a solution, the creatine compound is preferably dissolved in sterile saline solution at a concentration of about 5% cyclocreatine or homocyclocreatine.

The creatine compounds can be formulated with one or more adjuvants and/or pharmaceutically acceptable carriers according to the selected route of administration. The addition of gelatin, flavoring agents, or coating material can be used for oral applications. For solutions or emulsions in general, carriers may include aqueous or alcoholic/ aqueous solutions, emulsions or suspensions, including saline and buffered media. Parenteral vehicles can include sodium chloride, potassium chloride among others. In addition, intravenous vehicles can include fluid and nutrient replenishers, electrolyte replenishers among others.

Preservatives and other additives can also be present. For example, antimicrobial, antioxidant, chelating agents, and inert gases can be added (see, generally, Remington's Pharmaceutical Sciences, 16th Edition, Mack, (1980)).

Also, other compounds known in the art to inhibit or reduce thrombin induced platelet aggregation can be added to the creatine compound. Examples include, but are not limited to, bioflavonoids, such as quercetin and quercitin derivatives, and cyclooxygenase inhibitors, such as aspirin and other nonsteroidal anti-inflammatory drugs such as ibuprofen and nalproxen. Thrombolytic agents such as anisoylated plasminogen-streptokinase activator complex and tissue-type plasminogen activator, may also be added.

Creatine compounds can also be delivered directly to a site of endothelial damage by, for example, placing a catheter at the site of damage and slowly administering the creatine compound to the site through the catheter.

For example, creatine compounds can be used to prevent platelet aggregation at damaged endothelium caused by percutaneous transluminal coronary angioplasty. This procedure requires the placement of a balloon catheter in a coronary artery that is partially occluded. The inflation of the balloon expands the inner diameter of the artery, improving blood flow through the artery. However, the endothelium of the artery may be damaged by this procedure, resulting in the aggregation of circulating blood cells, including platelets, on the damaged cell wall. Following inflation of the balloon, creatine compounds delivered to the site via the catheter inhibit platelet aggregation on the artery wall, maintaining patency of the artery and reducing or preventing reocclusion.

Similarly, creatine compounds can be applied directly to the sites of artherotomy, reducing or preventing platelet aggregation, thrombosis, and occlusion.

Creatine compounds can also be used to reduce platelet aggregation on vascular prostheses such as vascular grafts, vascular stents, heart valves and other blood-contacting products such as catheters, blood dialysis membranes, tubing, etc., by coating such devices with the creatine compound. Such coating techniques are known in the heart. The efficacy of the coated device can be tested by assays known in the art, as described, for example, in U.S. Pat. No. 5,585,361, herein incorporated by reference in its entirety.

The present invention is demonstrated more fully by the following examples, which are not intended to be limiting in any way.

EXAMPLE 1

Inhibition of Platelet Aggregation by Cyclocreatine

Blood from healthy volunteers was collected in an anticoagulant citrate solution according to standard protocols. The whole blood/citrate solution was centrifuged at 200×g for 10 minutes to obtain platelet-rich plasma (PRP). The platelet count, as determined by Coulter Counter, was 2.88× $10^8$/mL. Aliquots (0.5 mL each) of the PRP were incubated with and without various concentrations of cyclocreatine (0 to 10 mM final concentration) for 30 minutes at room temperature. The aggregation assay was then carried out in the presence of thrombin (10 ul of thrombin was added to each aliquot, to a final concentration of 1 nM) with stirring at 37° C. using a Chrono-Log Whole Blood Aggregometer. (Chronolog Corp., Havertown, Pa.) Absorbance was measured at 500 nm. The results are shown in Table 1, below.

TABLE 1

| Aliquot No. | Cyclocreatine concentration | Thrombin concentration | % Aggregation of Platelets |
|---|---|---|---|
| 1 | 1 mM | 1 nM | 88 |
| 2 | 1 mM | 1 nM | 88 |
| 3 | 5 mM | 1 nM | 11 |
| 4 | 5 mM | 1 nM | 11 |
| 5 | 10 mM | 1 nM | 0 |
| 6 | 10 mM | 1 nM | 0 |
| 7 | 0 mM | 1 nM | 88 |

As can be seen in Table 1, the percentage of platelet aggregation dropped from 88% aggregation (with 0 to 1 mM cyclocreatine) to 0% aggregation (with 10 mM cyclocreatine) Aggregation was also inhibited by 5 mM cyclocreatine, with only 11% platelet aggregation.

Human umbilical vein cell contraction was also inhibited with cyclocreatine in vitro. Endothelial cells normally form a barrier on the inside of blood vessels to restrict passage of cells and macromolecules from the lumen to the interstitium. Thrombin induces actin stress fiber formation in endothelial cells which leads to intercellular gap formation and increased vascular permeability, a key inflammatory event during vessel or tissue injury.

Thrombin also causes secretion of inflammatory factors, prostacyclin, and expression of p-selectin. Although thrombin increases cytosolic calcium levels in endothelial cells, inhibition of calcium flux does not effect the cytoskeletal response. This suggests that, as in brain cells, calcium changes are not important for shape changes and may be part of a distinct signal transduction cascade.

As an initial screen for CKB function in endothelial cells, we quantitated the shape change and calcium responses to thrombin in primary cultures of human umbilical vein endothelial cells (HUVEC) and then studied the effect of cyclocreatine on these processes.

EXAMPLE 2

Inhibition of Endothelial Cell Contraction by Cyclocreatine

Primary cultures of pooled Human umbilical vein endothelial cells (HUVEC) cells were purchased from Clonetics (Walkersville, Md.) and cultured according to the manufacturer's protocol. About 2500 cells/cm$^2$ were cultured in Endothelial Cell Growth Medium BulletKit-2 (Clonetics, Walkersville, Md.) on collagen (Gibco, Grand Island, N.Y.) coated RS Lab Tek II slides for 5 days until confluent. Cells were then cultured in low serum (0.5%) medium overnight. Cells were treated with 50 mM cyclocreatine for 3 to 4 hours, or with 10 mM ROCK (Rho Kinase) inhibitor Y-27632 for 30 minutes, as described in Maekawa et al., (1999) *Science* 285: 895–8, hereby incorporated by reference in its entirety.

Thrombin was delivered at a final concentration of 10 pM for 20 minutes to endothelial cells. F-actin was stained with Alexa 594 phalloidin (Molecular Probes). HUVECs were examined under fluorescence and phase contrast micrography, and cells were scored as either round or flat.

To assay for intracellular calcium levels, cell media was decanted and replaced with Fluo-3 AM (Molecular Probes) in 100 ml of loading buffer with 1% Fetal Calf Serum (FCS) for 1 hour. Cells were rinsed with loading buffer and the 96-well plate was placed into a Fluorometric Imaging Plate Reader (FLIPR, Molecular Devices, Sunnyvale, Calif.). The relative intracellular calcium levels were monitored at 488 nM for 210 seconds in 4 to 8 identically treated wells. To monitor calcium release from intracellular stores thrombin was delivered in buffer containing 10 mM EDTA. Various phospholipase C inhibitors were applied as well.

Figure 7:
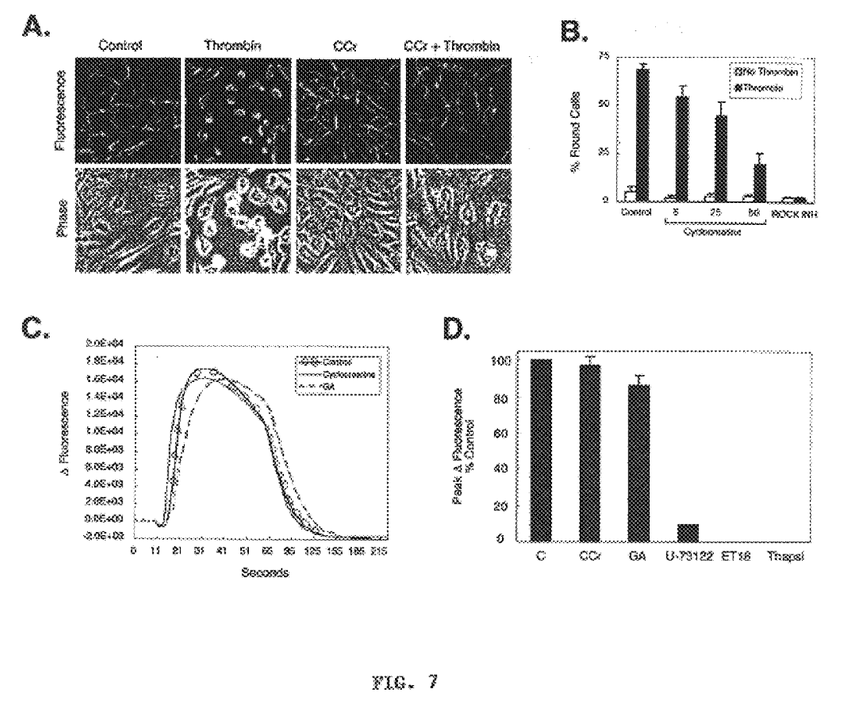
FIG. 7 shows CKB Inhibition in HUVEC Cells.

Confluent monolayers of HUVECs were stained with Alexa 594 phalloidin, and F-actin staining was detected primarily at the border of polygonal shaped cells, although fine actin filament fibers were apparent in many cells (FIG. 7A). Following treatment with thrombin most cells contracted into a round spherical shape that was heavily filled with F-actin and displayed membrane blebs. Cells that had not contracted displayed heavy stress fibers consistent with previous studies. The thrombin increase in F-actin stress fibers was readily apparent but is a subjective measure based on visual impression. Cell rounding effect, by contrast, is straight-forward to quantify. While only 2% of the cells were round in control cultures, after thrombin treatment 80% of the cells became round (FIG. 7B). As expected addition of the ROCK (Rho Kinase) inhibitor completely blocked the thrombin effect and only 2% of cells were round. Interestingly, cyclocreatine also displayed a dose-dependent protective effect (FIG. 7B). At the maximum dose of cyclocreatine, only 20% of the cells became round in response to thrombin. This suggests that CKB activity is important for thrombin mediated shape changes in HUVECs.

To determine the effect of cyclocreatine on calcium responses, HUVECs were examined by FLIPR. Thrombin elicited a sharp change in fluorescence corresponding to an increase in cytosolic calcium (FIG. 7C). This change was largely due to release of intracellular calcium stores (data not shown). The addition cyclocreatine had almost no effect on the calcium response (FIG. 7C, D). This suggests that CKB is not involved in PAR-1 calcium signaling. These findings suggest that CKB is part of a conserved signaling pathway leading to morphology changes. Just like the conserved elements RhoA, ROCK, myosin light chain kinase, and myosin phosphorylation, CKB may function in neurons, astrocytes, and endothelial cells to provide energy for pathway-specific signal transduction. The effect of cyclocreatine on calcium release is even less in endothelial cells than in neurons and astrocytes.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for inhibiting thrombin-induced platelet aggregation in a subject in need thereof, comprising administering to the subject a pharmaceutically effective amount of a creatine compound.

2. The method of claim 1, wherein the creatine compound is a creatine kinase inhibitor.

3. The method of claim 2, wherein the creatine kinase inhibitor is cyclocreatine.

4. The method of claim 2, wherein the creatine kinase inhibitor is homocyclocreatine.

5. The method of claim 1, wherein the creatine compound further comprises a bioflavonoid.

6. The method of claim 1, wherein the creatine compound further comprises a cyclooxygenase inhibitor.

7. A method according to claim 1 for treating stroke.

8. A method according to claim 1 for treating transient ischemia attacks.

9. A method according to claim 1 for treating myocardial infarction.

10. A method for inhibiting the aggregation of blood platelets in a mammal, comprising orally treating the mammal with a pharmaceutically effective amount of a creatine compound.

11. The method of claim 10, wherein the creatine compound is a creatine inhibitor.

12. The method of claim 10, wherein the creatine kinase inhibitor is cyclocreatine.

13. The method of claim 10, wherein the creatine kinase inhibitor is homocyclocreatine.

14. A method for treating a thrombotic condition in a mammal, the method comprising the administration of a therapeutic composition comprising a creatine compound to the mammal, in a dosage effective to inhibit the aggregation of platelets.

15. The method of claim 14, wherein the creatine compound is a creatine kinase inhibitor.

16. The method of claim 15, wherein the creatine kinase inhibitor is cyclocreatine.

17. The method of claim 15, wherein the creatine kinase inhibitor is homocyclocreatine.

18. The method of claim 14, wherein the thrombotic condition is venous thrombosis.

19. The method of claim 14, wherein the thrombotic condition is coronary artery thrombosis.

20. A method for promoting reperfusion of an artery or vein and inhibiting reocclusion, comprising administering to a subject in need thereof a creatine compound.

21. The method of claim 20, wherein the creatine compound is a creatine kinase inhibitor.

22. The method of claim 21, wherein the creatine kinase inhibitor is cyclocreatine.

23. The method of claim 21, wherein the creatine kinase inhibitor is homocyclocreatine.

24. A method of preventing the formation of a thrombus in a mammal at risk of developing thrombosis, the method comprising the intravenous administration to the mammal of a therapeutic composition comprising a creatine compound in a dosage effective to inhibit the aggregation of platelets.

25. The method of claim 24, wherein the mammal is at increased risk of developing a thrombus due to a medical condition which disrupts hemostasis.

26. The method of claim 25, wherein the medical condition is heparin induced thrombocytopenia.

27. The method of claim 25, wherein the medical condition is coronary artery disease.

28. The method of claim 25, wherein the medical condition is atherosclerosis.

29. The method of claim 24, wherein the mammal is at increased risk of developing a thrombus due to a medical procedure.

30. The method of claim 29, wherein the medical procedure is cardiac surgery.

31. The method of claim 29, wherein the medical procedure is a cardiopulmonary bypass.

32. The method of claim 29, wherein the medical procedure is a catheterization.

33. The method of claim 32, wherein the catheterization is cardiac catheterization.

34. The method of claim 33, wherein the catheterization is percutaneous transluminal coronary angioplasty.

35. The method of claim 29, wherein the medical procedure is atherotomy.

36. The method of claim 29, wherein the medical procedure involves placement of a prosthetic device.

37. The method of claim 36, wherein the prosthetic device is a cardiovascular valve.

38. The method of claim 36, wherein the prosthetic device is a vascular graft.

39. The method of claim 36, wherein the prosthetic device is a stent.

40. The method of claim 24, wherein the creatine compound is a creatine kinase inhibitor.

41. The method of claim 40, wherein the creatine kinase inhibitor is cyclocreatine.

42. The method of claim 40, wherein the creatine kinase inhibitor is homocyclocreatine.

43. The method of claim 14, wherein the creatine compound is administered after treatment with a thrombolytic agent.

44. The method of claim 14, wherein the creatine compound is administered concurrently with a thrombolytic agent.

45. A method of inhibiting the aggregation of platelets on the surface of a prosthetic device comprising coating the device with a creatine compound in an amount sufficient to inhibit the aggregation of the platelets on the surface prior to exposure of the device to the platelets.

46. The method of claim 45, wherein the creatine compound is a creatine kinase inhibitor.

47. The method of claim 46, wherein the creatine kinase inhibitor is cyclocreatine.

48. The method of claim 46, wherein the creatine kinase inhibitor is homocyclocreatine.

49. The method of claim 45, wherein the prosthetic device is a coronary valve.

50. The method of claim 45, wherein the prosthetic device is a stent.

51. The method of claim 45, wherein the prosthetic device is a vascular graft.

* * * * *